(12) United States Patent
McCoy (10) Patent No.: US 11,363,837 B2
(45) Date of Patent: Jun. 21, 2022

(54) MODULAR SMOKING DEVICE

(71) Applicant: David McCoy, Hudson, FL (US)

(72) Inventor: David McCoy, Hudson, FL (US)

( * ) Notice: Subject to any disclaimer, the term of this patent is extended or adjusted under 35 U.S.C. 154(b) by 127 days.

(21) Appl. No.: 15/872,508

(22) Filed: Jan. 16, 2018

(65) Prior Publication Data
US 2019/0246691 A1    Aug. 15, 2019

(51) Int. Cl.
*A24F 1/24* (2006.01)
*H05B 7/18* (2006.01)
*A24F 40/20* (2020.01)
*A24D 1/14* (2006.01)
*A24F 1/28* (2006.01)
*A24F 1/32* (2006.01)
(Continued)

(52) U.S. Cl.
CPC .............. *A24F 1/24* (2013.01); *A24B 15/16* (2013.01); *A24D 1/14* (2013.01); *A24F 1/06* (2013.01); *A24F 1/28* (2013.01); *A24F 1/30* (2013.01); *A24F 1/32* (2013.01); *A24F 40/50* (2020.01); *A61J 1/035* (2013.01); *A61M 15/0048* (2014.02); *A61M 15/06* (2013.01); *B65D 75/36* (2013.01); *H05B 7/18* (2013.01); *A24F 40/20* (2020.01); *A24F 40/48* (2020.01); *A61M 2205/123* (2013.01); *A61M 2205/3653* (2013.01); *A61M 2205/8206* (2013.01)

(58) Field of Classification Search
CPC .............................. A24F 1/24; A61M 15/0048
USPC ........................................................ 131/173
See application file for complete search history.

(56) References Cited

U.S. PATENT DOCUMENTS 3,381,158 A * 4/1968 Burhorn .................. H05H 1/48
　　　　　　　　　　　　　　　　　　　　　314/136
3,918,464 A * 11/1975 Kolodziej ................ A24F 1/30
　　　　　　　　　　　　　　　　　　　　　131/173
(Continued)

FOREIGN PATENT DOCUMENTS

CN        203952435 U  *  11/2014

OTHER PUBLICATIONS

Machine Translation of 203952435 (Year: 2014).*

*Primary Examiner* — Kelly M Gambetta
*Assistant Examiner* — Russell E Sparks
(74) *Attorney, Agent, or Firm* — Georgiy L. Khayet (57) ABSTRACT

Modular smoking devices that vaporize certain materials, such as tobacco or cannabis are disclosed. The technology provides for intelligent ignition, combustion, or vaporization of given material at the appropriate temperatures that prevent generation of harmful and unwanted byproducts. According to one embodiment, the modular smoking device comprises a self-contained combustion chamber to hold the material, a combustion mechanism integrated with the self-contained combustion chamber, and an energy source, such as a rechargeable battery, to power the combustion mechanism. The combustion mechanism is configured to provide targeted combustion of the material, where the active ingredients generated upon the combustion are consumed by inhaling a smoke or vapor resulting from the combustion or vaporization. The self-contained combustion chamber includes a lighterless combustion mechanism such as a piezoelectric lighter or a lighter sold under TESLA COIL LIGHTERS® that is designed to arc an electric discharge through the material in the self-contained combustion chamber.

18 Claims, 8 Drawing Sheets

(51) Int. Cl.
*A24F 1/30* (2006.01)
*A24B 15/16* (2020.01)
*B65D 75/36* (2006.01)
*A61M 15/00* (2006.01)
*A61M 15/06* (2006.01)
*A24F 1/06* (2006.01)
*A61J 1/03* (2006.01)
*A24F 40/50* (2020.01)
*A24F 40/48* (2020.01)

(56) References Cited

U.S. PATENT DOCUMENTS

| | | | |
|---|---|---|---|
| 7,186,958 B1* | 3/2007 | Nelson | A61M 11/042 |
| | | | 219/533 |
| 9,687,025 B2* | 6/2017 | Cyphert | A24F 1/00 |
| 10,238,146 B2* | 3/2019 | Nedelman | A24F 47/008 |
| 10,266,287 B2* | 4/2019 | Fulcher | B65B 61/06 |
| 10,272,454 B2* | 4/2019 | Mayer | B05B 5/16 |
| 10,561,172 B2* | 2/2020 | Armoush | H05B 6/105 |
| 2018/0332890 A1* | 11/2018 | Tweedie | A24F 7/00 |

\* cited by examiner

MODULAR SMOKING DEVICE

TECHNICAL FIELD

This disclosure generally relates to smoking devices. More particularly, this disclosure relates to modular smoking devices having a self-contained, self-powered combustion or vaporization chamber.

DESCRIPTION OF RELATED ART

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section.

Smoking and inhalation devices are well known for providing flavored vapor from a smokeable material to a user for therapeutic purposes or smoking pleasure. Some common smoking devices include a smoking pipe, a cigarette holder, a tobacco pipe, a bong, a water pipe, an electronic cigarette (e-cigarette), and a vaporizer. Traditionally, the smoking devices lack temperature control over combustion of tobacco, plant, or other smokeable materials. As such, research shows that these devices can produce unwanted, harmful, and potentially toxic byproducts upon inappropriately combusting the smokeable materials. Although there were some attempts to solve that problem, such as by introducing filters, there are still no efficient and cost-effective solutions.

SUMMARY

This section is provided to introduce a selection of concepts in a simplified form that are further described below in the Detailed Description section. This summary is not intended to identify key features or essential features of the claimed subject matter, nor is it intended to be used as an aid in determining the scope of the claimed subject matter.

This disclosure relates to modular smoking devices that generate smoke and vapors by combustion or vaporization of certain materials, such as tobacco, cannabis, or any other plant or herbal substances, for user's consumption. The main principles of the instant technology are equally applicable to a wide range of smoking devices, including, for example, smoking pipes, bongs, e-cigarettes, vaporizers, and the like. The technology provided allows for intelligently igniting, combusting, or vaporizing a given material at appropriate temperatures that may prevent generation of harmful and unwanted byproducts. That is achieved by regulating the energy used to heat, ignite, combust, or vaporize the materials.

According to one aspect of this technology, there is provided a modular device for combustion of a material having certain active ingredients for human consumption. The device comprises a self-contained combustion chamber to hold the material and a combustion mechanism integrated with the self-contained combustion chamber. The combustion mechanism is configured to provide targeted combustion of the material, where the active ingredients generated upon the combustion are consumed by inhaling a smoke resulting from the combustion. The device also includes an energy source, such as a rechargeable battery, to power the combustion mechanism.

In certain embodiments, the device also includes a smoking pipe to facilitate inhalation of the smoke and that incorporates the self-contained combustion chamber and the combustion mechanism. The smoking pipe may include a plurality of mouthpiece receptacles for simultaneous consumption of the active ingredients by a plurality of users. The smoking pipe is constructed to have any suitable shape and made of any suitable material, such as aluminum, stainless steel, polymer material, glass, wood, or a metal alloy.

The self-contained combustion chamber incorporates a flameless or lighterless combustion mechanism, which includes two or more electrodes designed to arc an electric discharge through the material in the self-contained combustion chamber. For example, the lighterless combustion mechanism includes a piezoelectric lighter or a lighter sold under TESLA COIL LIGHTERS®. Alternatively, a heating mechanism may generate infrared radiation, conduction, or induction through an appropriate contact medium. The device may also include one or more electronic modules, including a programmable electronic control unit to control an amount of electric power provided by the energy source to the lighterless combustion mechanism and one or more input/output units. The programmable electronic control unit is designed to intelligently control the lighterless combustion mechanism to cause generation of a predetermined amount of heat that is selected to efficiently combust the material based on an amount of the material and a type of the material, and to create a predetermined dosage of the active ingredients. The input/output units can include one or more switches, buttons, regulators, user controls, and at least one of the following indicators: an activation indicator, a low energy source indicator, an electrical connection indicator, and a mode of operation indicator.

In certain embodiments, the material for combustion can be provided in a blister pack of prepackaged doses of the material. The device can be designed to receive the blister pack, and individually and independently combust the prepackaged doses upon user's instruction. In the alternative, the self-contained combustion chamber can optionally include a material basket to facilitate manual dosage of the material. In yet more embodiments, the device can also comprise a water filtration mechanism to separate the active ingredients in the smoke from undesirable byproducts. Moreover, the device can include a safety lockout feature to prevent accidental activation of the self-contained combustion mechanism. The device may also include a timer for automatic shutoff.

In another aspect of this disclosure, there is provided a modular device for vaporizing of a material having active ingredients for human consumption. This device comprises a self-contained vaporization chamber to hold the material, a vaporization mechanism integrated with the self-contained vaporization chamber, and an energy source to power the vaporization mechanism. The vaporization mechanism is configured to provide targeted vaporization of the material, where upon the vaporization of the material, the active ingredients are consumed by inhaling a vapor resulting from the vaporization process. Like the combustion chamber mentioned above, the self-contained vaporization chamber is configured to create targeted heat to induce the vaporization. The heating device is programmable to create an amount of heat measured to heat the self-contained vaporization chamber to a predetermined temperature based on an amount of the material and a type of the material to efficiently vaporize the material.

Additional objects, advantages, and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

Embodiments are illustrated by way of example and not limitation in the figures of the accompanying drawings, in which like references indicate similar elements and in which.

DETAILED DESCRIPTION OF EXAMPLE EMBODIMENTS

The following detailed description of embodiments includes references to the accompanying drawings, which form a part of the detailed description. Approaches described in this section are not prior art to the claims and are not admitted to be prior art by inclusion in this section. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and operational changes can be made without departing from the scope of what is claimed. The following detailed description is, therefore, not to be taken in a limiting sense, and the scope is defined by the appended claims and their equivalents.

The consumption of tobacco, cannabis, and related products is dynamically changing and will continue changing over the next several years. This is due mainly to adoption of new legalization and medical benefits of cannabis and derivatives of cannabis. Currently, most cannabis production is on a less than scientific basis. Cannabis is grown using many different methods depending on the legal status of the material in the area or province where it is grown. In states or provinces where it is illegal, growing takes place in clandestine "guerilla" grows. In places where cannabis is legal, however, growing takes place both outdoors and indoors in more controlled environments. In both legal and clandestine growing operations, the methods of cultivation and curing creates results that can vary widely. This creates a product of varying strengths and percentages of active ingredients.

Some strains of cannabis are designed for control of epileptic seizures, some for pain relief, some to increase appetites, some to make people sleepy, and some for cerebral excitation. All types have been used for decades by both medically qualified marijuana patients and recreational users.

In the future, the production, packaging, and distribution of cannabis readily resemble processes in the pharmaceutical industry, and follow many of the same manufacturing, packaging, and distribution protocols. For example, according to the embodiments of this disclosure, cannabis can be packaged into individual and uniform dose capsules, blisters, and the like. Such packaging provides uniform and consistent product offering, expectable dosage, repeatable user results, longer shelf life, and a hygienically superior, cleaner, and purer consumable product. By creating and standardizing cannabis production and methods for test and quality control, the user will receive a product that is designed and targeted to provide a repeatable, maximum chemical delivery while removing or diminishing inactive ingredients and byproducts of the production process. To this end, the embodiments of this disclosure concern a modular device that provides different methods and procedures for consumption. These methods provide for a more efficient and effective ingestion of cannabis, derivatives of cannabis, tobacco, and similar products. The device can be used in a home, office or treatment center, in the field, and at remote locations.

Generally, the embodiments of this disclosure are concerned with various modular smoking devices that generate vapors of selected materials, such as tobacco or cannabis. The technology provides for intelligent ignition, combustion, and vaporization of a given material at substantially lower, targeted temperatures that prevent generation of harmful and unwanted byproducts. According to one embodiment, the modular device comprises at least a self-contained combustion chamber to hold the material, a combustion mechanism integrated with the self-contained combustion chamber, and an energy source, such as a rechargeable battery, to power the combustion mechanism. The self-contained combustion chamber includes a lighterless combustion mechanism (as used herein, "lighterless" means a combustion mechanism that is "lighter-free", i.e. has no lighter) such as a piezoelectric lighter or a lighter sold under TESLA COIL LIGHTERS® that is designed to arc an electric discharge through the material in the self-contained combustion chamber. Alternatively, the heating mechanism may generate heat through radiation, conduction, or induction through an appropriate contact medium. The material for combustion is placed into a material basket of the self-contained combustion chamber, which allows for the arcing of the electric charge used for combustion or the introduction of regulated heat via induction or conduction.

The modular device can be integrated into a smoking pipe, tobacco pipe, e-cigarette, bong, vaporizer, or any other suitable smoking/inhalation apparatus. The modular device may be connected to or include certain input units, such as buttons or switches, to control the operation of the device and certain output units, such as light emission diodes (LEDs) for showing activation, low battery, electrical connection, and mode of operation.

The smoking pipe has the feature of disassembly for cleaning and maintenance. Also, there can be provided one or more mouthpiece receptacles ("pipe lips") that allow for multiple users to share the same smoking pipe. In certain embodiments, the modular device is also capable for use with a traditional flame if the combustion mechanism is inoperative. A safety lockout feature is also incorporated to insure accidental activation of the smoking pipe is avoided. For example, a two-stage switch can be used to implement the safety lockout feature. A countdown timer may also be integrated for automatic shutoff.

The shape and geometry of the modular device, including the combustion chamber, can vary. For example, it can be of a tubular or cylindrical shape. The combustion chamber can have one or more arcing electrodes sold under TESLA COIL LIGHTERS® which pass an electric current through the material held in a material basket (or screen) in the combustion chamber (or, alternatively, the heating mechanism may generate infrared radiation, conduction or induction through an appropriate contact medium), causing ignition and combustion, resulting in a smoke that is pulled through the combustion chamber and into the smoking pipe throat to either the user, via vacuum created by puffing on the smoking pipe, or to a secondary device being either a water filtration unit or a holding chamber for distribution.

The smoking pipe may be constructed of aluminum, stainless steel, polymer material, other metal alloy, wood, glass, or any combination thereof. The materials of construction are durable, chemically resistant to cleaning solvents (primarily isopropyl alcohol), and have replaceable components. The materials used in the modular device and smoking pipe do not give off harmful byproducts related to, or created by, the act of combustion or vaporization.

A secondary method of ingestion includes a vaporization chamber, which is used in the modular device instead of the combustion chamber. The vaporization chamber creates the targeted heat required to induce vaporization. The vaporization device will have the same user and safety features of the combustion type lighterless pipe as discussed above. Electrical current will heat the material for combustion in the material basket to the required temperature for use. Connections between the smoking pipe components (e.g., a pipe stem) and the modular device (including the combustion or vaporization chamber) employ a quarter turn locking feature for easy use and disassembly by all users. For example, quick connect Murphy proof connectors can be used.

As mentioned above, the modular device can be used in many various smoking apparatuses, including a bong, a water pipe, an e-cigarette, and so forth. In case of implementation as a bong, bong connection allows for the combustion chamber to be easily connected to a bong device (for example, via the quarter turn easy on connection). The smoke stream is pulled through the combustion chamber and a pipe of the bong device into a water filtration chamber. The combustion chamber can be separated from the discharge end by baffles to reduce the incidence of water droplets from being entwined in the smoke stream. The bong device also includes a carburetor and features that allow for disassembly, cleaning, replacement of parts, and reassembly by all users.

The water pipe provides an alternative to the bong device for those who prefer that method of consumption. The water pipe allows for connection of the combustion chamber, a water filled chamber through which the smoke stream passes, baffles to prevent water from mixing into the smoke stream, and a discharge pipe with mouthpiece capability. The structure of water pipe also provides for disassembly, cleaning, replacement, and reassembly by users of all ages.

In additional embodiments, the modular device can include a pump. The pump (or a pump device) provides for attachment of the combustion chamber with a check valve at the attachment point, and a discharge port, with a check valve, for release of the smoke stream. The pump allows for the expansion of the chamber volume to create a vacuum that pulls the smoke stream into the pump chamber. The chamber also provides for the temporary storage of smoke or vapor for use. Subsequent collapsing of the chamber discharges the smoke either to a mouthpiece receptacle for ingestion, or into a secondary stage of water filtration for temperature reduction, filtration, and finally ingestion. The pump can also be used after the water filtration stage to allow for filtered smoke to fill the pump cavity for discharge.

Yet another embodiment involves an electric motor turbine. The electric motor provides the necessary flow of air for patients that cannot create a vacuum on their own. The turbine works for a short duration, long enough to fill the smoke or combustion chamber, or continuously for a steady stream of smoke, until the activation switch is released. Similarly, to above, the smoke can be directed to a water filtration device, into a chamber for sharing, or directed outward for use by inhalation.

As mentioned earlier, the material for combustion can include cannabis, cannabis derivatives, tobacco, herb products, or any other plant-based products. The material can be in a naturally occurring plant form or in a pelletized pharmaceutical form. Preferably, the material is one that has been grown, dried, cured, and processed with scientific methods and prepared for storage to promote long shelf life and reduced incidence of mold and other detrimental organisms. The material can be processed to remove targeted harmful chemical compounds from the plant material, segregate the desired resins, store them in a hygienic device, and mix it with enough material to create a balanced, measured dosing of the chemical. These individual doses of material are packaged to provide dosing that allows for individual "hits" or larger doses for larger users, or groups. By segregating the different parts of the plant, i.e., retaining only the chemically active portions (e.g., the resins), there is the benefit of the desired portion of the plant, while reducing or removing the unnecessary or undesirable portions of the plant material. This make for a cleaner, safer, healthier product. This also requires less material and less expense, and results in fewer harmful elements in a smoke stream, improved logistics, and greater efficiencies. The doses can be packaged for individual use, extended use, different effects (different strains), flavors, or for specific recommended medical dosing. The packaging can include blister packs, or other hygienic pharmaceutical grade packaging. Product selection could include flavoring, adding other plant or doctor recommended chemicals, or adding nicotine.

The embodiments of this disclosure will be now presented with reference to the accompanying drawings of modular smoking devices. For purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

It should be also understood that the terms "first," "second," "third," and so forth can be used herein to describe various elements. These terms are used to distinguish one element from another, but not to imply a required sequence of elements. For example, a first element can be termed a second element, and, similarly, a second element can be termed a first element, without departing from the scope of present teachings.

Moreover, it shall be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," and so forth). Spatially relative terms, such as "beneath," "below," "lower," "above," "upper," and the like may be used to describe an element or feature's relationship to another element(s) and/or feature(s) as, for example, illustrated in the drawings. It shall be appreciated that the spatially relative terms are intended to encompass different orientations of the modular device or its elements in use in addition to the orientation depicted in the figures. For example, if the modular device display or any of its components in the drawings is turned over, elements described as "below" and/or "beneath" other elements or features would then be oriented "above" the other elements or features. The modular device or its components may be otherwise oriented (e.g., rotated 90 degrees or at other orientations) and the spatially relative descriptors used herein interpreted accordingly.

The term "material" shall be construed to mean a product, such as an herb-based or plant-based substance, which is suitable for generation of smoke or vapor upon heating, burning, igniting, or combusting. Some examples of the material include tobacco, cannabis, and derivatives of cannabis. The material can be provided in a solid, semi-solid, or liquid form. In some embodiments, the material can be prepackaged in "doses." For example, a blister pack having multiple doses of material can be provided.

The term "modular" shall be construed to mean that one or more components make up a unitary structure upon their arrangement, connection, or joining. For example, a modular device means that it includes two or more components that can be interconnected to make up a unitary structure.

The term "combustion chamber" refers to a confined or open space where a material can be placed and ignited, burned, heated, or combusted (e.g., using an electric discharge). Similarly, the term "vaporization chamber" refers to a confined or open space where a material can be placed and vaporized, for example, using a heating device. The term "vaporization" means the phenomenon that a solid or liquid form of material is converted into a gas (vapor) for further user's consumption.

The embodiments are described with reference to the drawings. The drawings are schematic illustrations of idealized example embodiments. As such, variations from the shapes of the illustrations as a result, for example, of manufacturing techniques or tolerances, are to be expected. Thus, example embodiments discussed herein should not be construed as limited to the particular shapes of regions illustrated herein but are to include deviations in shapes that result, for example, from manufacturing or learned "best practices".

Figure 1:
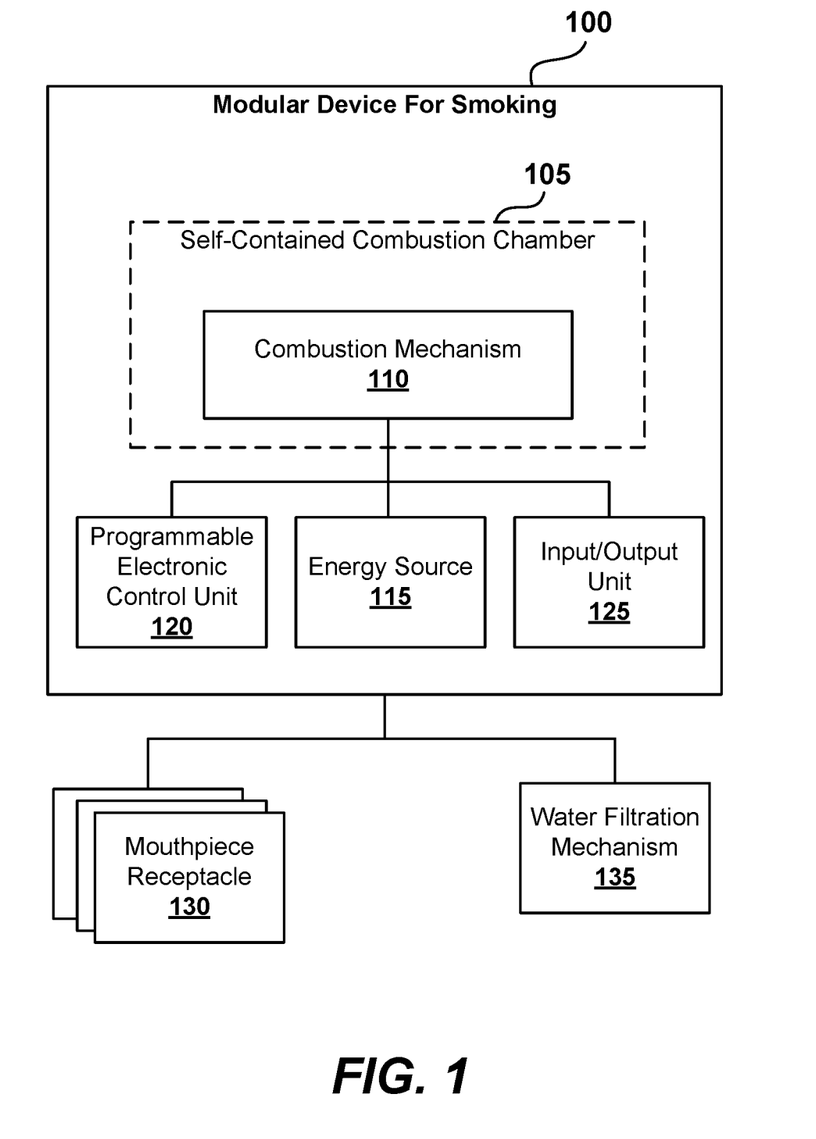
FIG. 1 is high-level block diagram of a modular device including a self-contained combustion chamber, according to one embodiment.

FIG. 1 shows a high-level block diagram of a modular device 100, according to one example embodiment. Modular device 100 is designed to ignite and combust a material, which can be either in a bulk or prepackaged form and includes an herb or plant-based smoking substance. Upon combustion of the material, active ingredients of the material are combusted for user consumption, which consists of inhaling a smoke resulting from the combustion. Modular device 100 can be an integral part of a larger device to facilitate inhaling of the smoke resulting from the combustion of the material. For example, modular device 100 can be integrated in a smoking pipe, smoking pump, bong, e-cigarette, and the like.

Modular device 100 includes a self-contained combustion chamber 105 to receive and hold the material. For example, self-contained combustion chamber 105 is designed to receive a prepackaged dose of the material, where the prepackaged dose is provided in a blister pack. As such, self-contained combustion chamber 105 can be an open or confined space suitable for inserting the material inside thereof. For example, self-contained combustion chamber 105 may be an open container, or may have a lid with engineered "bleed air" holes to allow a regulated airflow for maximum efficiency.

Modular device 100 also includes a combustion mechanism 110 that is integrated with self-contained combustion chamber 105. Combustion mechanism 110 is configured to provide targeted combustion of the material. For these ends, combustion mechanism 110 includes a lighterless combustion mechanism. In one embodiment, the lighterless combustion mechanism includes two or more electrodes designed to arc an electric discharge through the material inside self-contained combustion chamber 105. Respectively, the electrodes are driven by a piezoelectric lighter or a lighter sold under TESLA COIL LIGHTERS®, which can be integrated into combustion mechanism 110. In certain embodiments, there are provided two or more lighters sold under TESLA COIL LIGHTERS®. The electrodes are spaced apart so as to generate one or more electric arcs through different parts of the material. In the alternative, the electrodes are arranged so as to generate one or more electric arcs through the same part of the material. If there are several piezoelectric lighters or lighters sold under TESLA COIL LIGHTERS® provided, each of them can be of different level of power. Furthermore, each of the piezoelectric or lighters sold under TESLA COIL LIGHTERS® can be individually controlled and be activated at different times. Alternatively, the heating mechanism may be in the form of infrared radiation, conduction, or induction through an appropriate contact medium designed to provide the same results as the electric arcs.

Modular device 100 also includes an energy source 115 to power combustion mechanism 110. The energy source 115 may include a replaceable or non-replaceable battery or accumulator, rechargeable battery, or non-rechargeable battery. The energy source 115 may also contain a resistive-capacitive circuit for rapid discharge of stored electric power to advance rapid heating of the modular device 100. The energy source 115 may include an interface for plugging into a power adapter or a power source. In some embodiments, there can be installed a wireless charging module to enable wireless charging of the energy source.

Modular device 100 optionally includes a programmable electronic control unit 120 to control an amount of electric power provided by the energy source to the combustion mechanism 110. Programmable electronic control unit 120 can be implemented as a controller, processor, microprocessor, Central Processing Unit (CPU), processor array, or logic circuit. A programmable electronic control unit 120 can include a memory to store software, middleware, or firmware that includes operation instructions. As such, the instructions can cause operation of the device as described herein. Particularly, the instructions can direct combustion mechanism 110 to create a predefined amount of heat in response to a command provided by programmable electronic unit 120. The amount of heat can be intelligently and dynamically selected to efficiently combust the material based on an amount of the material and a type of the material, and to create a predetermined dosage of active ingredients. The amount of material can be predetermined if the material is prepackaged. In some embodiments, the user can make an input to identify the amount of material he uses. In some embodiments, modular device 100 can be configured to sense or measure the amount of material by a built-in sensor. Similarly, the type of material can be either provided to programmable electronic unit 120 by a user's input or it can be automatically identified by a built-in sensor. In case of the sensor, prepackaged doses can include physical or visual marks that can be read by the sensor to determine the type or amount of the material.

In various embodiments, programmable electronic unit 120 sends one or more commands to combustion mechanism 110 not only to ignite the material, but also to keep it combusting at a predetermined speed. Furthermore, programmable electronic unit 120 directs combustion mechanism 110 such that the material is combusted at a relatively low temperature so as to minimize or eliminate the production of harmful byproducts. In certain additional embodiments, there can be a built-in temperature sensor to facilitate the control of the combustion by programmable electronic unit 120.

In the embodiments where one piezoelectric lighter or one lighter sold under TESLA COIL LIGHTERS® is provided, programmable electronic unit 120 can control the timing of the lighter's operation. Programmable electronic unit 120 can also control the strength of discharge created by the piezoelectric lighter or the lighter sold under TESLA COIL LIGHTERS®. When multiple piezoelectric or lighters or lighters sold under TESLA COIL LIGHTERS® are installed, programmable electronic unit 120 can control the activation/deactivation times and the power of each individual lighter separately. As such, programmable electronic unit 120 can independently turn on and turn off the lighters in a predetermined fashion or as instructed by the user. Alternatively, the heating mechanism may generate infrared, conduction or induction through an appropriate contact medium designed to provide the same results as the electric arcs.

Still referring to FIG. 1, modular device 100 further comprises an input/output unit 125. The input elements of unit 125 can include buttons, switches, regulators, sensor panels, electronic ports, terminals, radio communication interface, wireless communication interface, wired communication interface, optical communication interface, and so forth. The output elements of unit 125 can include LEDs, displays, tactile (haptic) feedback devices, and the like. For example, the LEDs can include an activation indicator, a low energy source indicator, an electrical connection indicator, and a mode of operation indicator.

As mentioned earlier, modular device 110 can further include one or more mouthpiece receptacles 130. For example, there can be provided a plurality of mouthpiece receptacles 130 for simultaneous consumption of the active ingredients of the material by a plurality of users. Mouthpiece receptacles 130 are designed to be removably attached to modular device 100 or any of its components.

In additional implementations, modular device 110 can be further operatively coupled to a water filtration mechanism 135 to separate the active ingredients in the smoke from undesirable byproducts. In other words, water filtration mechanism 135 can be removably connected between self-contained combustion chamber 105 and mouthpiece receptacle 130 to filter the smoke generated by the material placed in combustion chamber 130.

Figure 2:
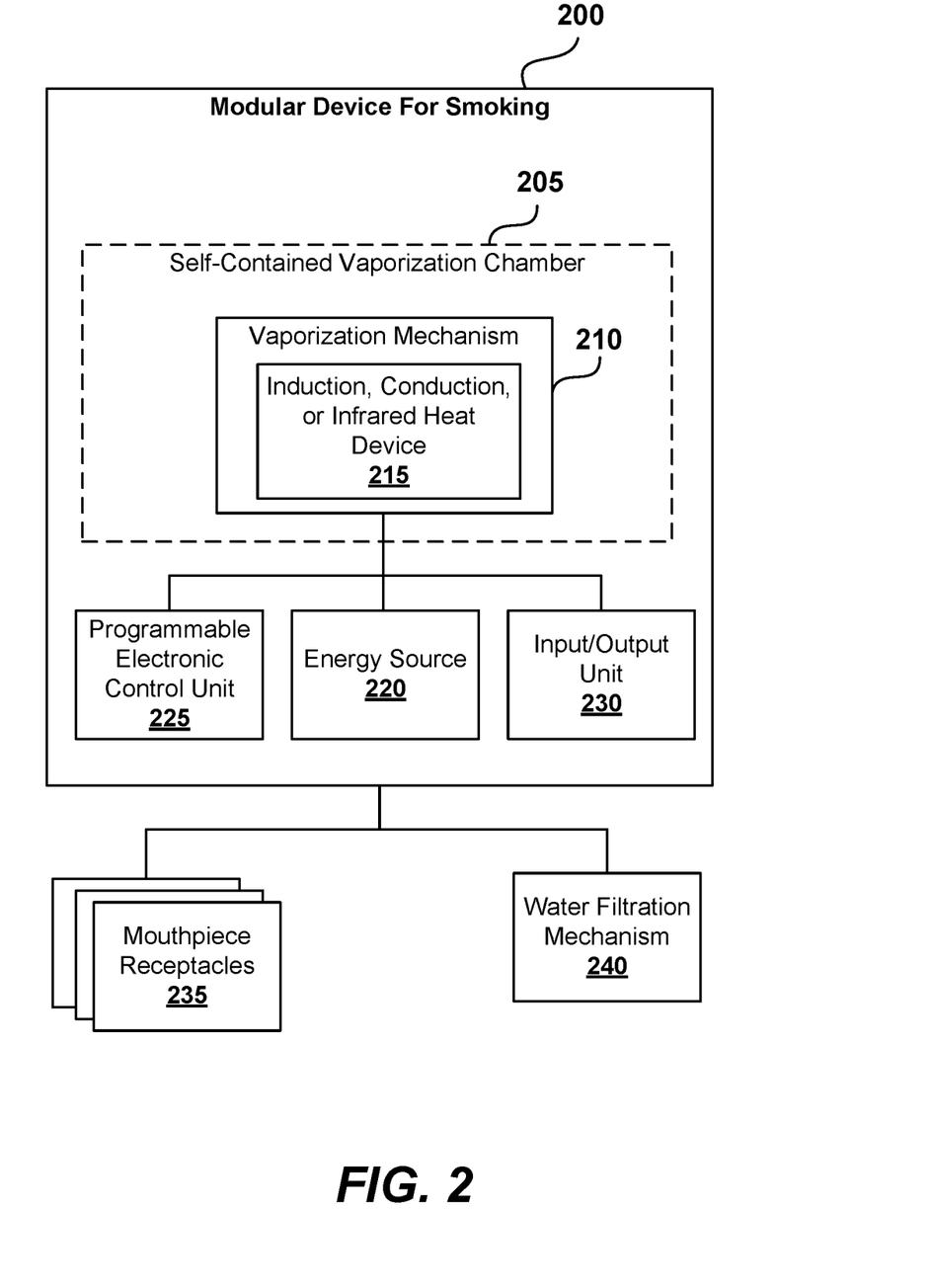
FIG. 2 is high-level block diagram of a modular device including a self-contained vaporization chamber, according to another embodiment.

FIG. 2 shows a high-level block diagram of a modular device 200, according to another embodiment. Modular device 200 is substantially similar to modular device 100, except the combustion chamber is now replaced with a self-contained vaporization chamber 205. Self-contained vaporization chamber 205 is configured to hold the material for further vaporization of its active ingredients. Upon vaporization of active ingredients, they can be consumed by a user by inhaling a vapor resulting from the vaporization. Modular device 200 can be an integral part of a larger device to facilitate inhaling of the smoke/vapor. For example, modular device 200 can be integrated in a smoking pipe, smoking pump, bong, e-cigarette, and the like.

A vaporization mechanism 210 is provided and is integrated with self-contained vaporization chamber 205. Vaporization mechanism 210 is designed to provide targeted vaporization of the material when it is powered by an energy source 220. Energy source 220 includes a rechargeable battery or any other suitable electric power source. When powered, self-contained vaporization chamber 205 creates targeted heat to induce the vaporization of active ingredients of the material using an induction, conduction, or infrared heat device 215.

Induction, conduction, or infrared heat device 215 can be integrated into or connected to vaporization mechanism 210. Induction, conduction, or infrared heat device 215 is also programmable to create a measured amount of heat to heat self-contained vaporization chamber 205 to a predetermined temperature based on an amount of the material and a type of the material to efficiently vaporize the material.

Modular device 200 optionally includes a programmable electronic control unit 225 to control an amount of electric power provided by energy source 220 to vaporization mechanism 210. One example of programmable electronic control unit 225 includes a controller, processor, microprocessor, or logic circuit. Programmable electronic control unit 225 can include a memory to store software, middleware, or firmware that can cause operation of modular device 200 in a manner as described herein. For example, the instructions can direct vaporization mechanism 210 to create a predetermined amount of heat in response to a command provided by programmable electronic unit 225. The amount of heat can be selected to efficiently vaporize the material based on an amount of the material and a type of the material, and to create a predetermined dosage of active ingredients. The amount of material can be predetermined if the material is prepackaged in a known manner. In some embodiments, the user makes an input indicating the amount and type of material. In other embodiments, modular device 200 includes a built-in sensor configured to sense, measure, or otherwise identify the amount and type of material.

In certain embodiments, programmable electronic unit 225 sends commands to vaporization mechanism 210 to keep vaporizing the material at a predetermined pace and for a predetermined time. Furthermore, programmable electronic unit 225 controls the operation of vaporization mechanism 210 such that the material is vaporized at a relatively low temperature so as to minimize or eliminate production of harmful byproducts. In certain additional embodiments, there can be a built-in temperature sensor to control the vaporization of the material by programmable electronic unit 225.

Still referring to FIG. 1, modular device 200 further comprises an input/output unit 230. The input elements of unit 230 can include buttons, switches, regulators, sensor panels, electronic ports, terminals, radio communication interface, wireless communication interface, wired communication interface, optical communication interface, and so forth. The output elements of unit 230 can include LEDs, displays, tactile (haptic) feedback devices, and the like. For example, the LEDs can include an activation indicator, a low energy source indicator, an electrical connection indicator, and a mode of operation indicator.

Modular device 210 can further include one or more mouthpiece receptacles 235. For example, there can be provided a plurality of mouthpiece receptacles 235 for simultaneous consumption of the active ingredients of the material by a plurality of users. Mouthpiece receptacles 235 are designed to be removably attached to modular device 200 or any of its components.

Modular device 210 can be also connected to an optional water filtration mechanism 240 to separate the active ingredients in the smoke from undesirable byproducts. Water filtration mechanism 240 can be removably connected between self-contained vaporization chamber 205 and mouthpiece receptacle 235 to filter the smoke generated by the material placed in self-contained vaporization chamber 205.

Figure 3A:
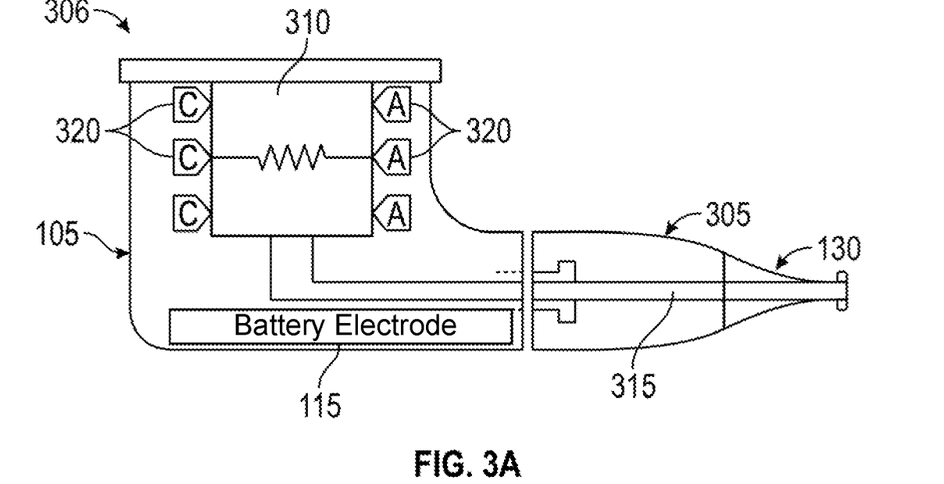
FIG. 3A is a simplified side view of a smoking pipe, according to one embodiment.

FIG. 3A is a simplified side view of a smoking pipe 300, according to one embodiment. Smoking pipe 300 includes a pipe stem 305, a mouthpiece receptacle 130, and self-contained combustion chamber 105. As shown in the figure, these elements are assembled into a unitary apparatus to facilitate smoking of the material. Elements of smoking pipe 300 are constructed of at least one of the following materials: aluminum, stainless steel, polymer material, and a metal alloy. Each of pipe stem 305, mouthpiece receptacle 130, and self-contained combustion chamber 105 includes an internal tube 315 for transporting smoke generated in self-contained combustion chamber 105 towards the user for inhalation.

FIG. 3A illustrates that self-contained combustion chamber 105 includes a material basket 310 designed to receive the material in bulk or prepackaged form. Material basket 310 has an open container shape where two or more electrodes 320 are exposed at the side walls. Electrodes 320 are a part of piezoelectric lightning devices or lighting devices sold under TESLA COIL LIGHTERS® that are powered by an energy source 115. Smoking pipe 300 can further comprise a safety lockout feature to prevent accidental activation of self-contained combustion chamber 105. Once electrodes 320 create an electric discharge, it ignites the material placed in material basket 310 and causes generation of smoke. The smoke is further transported through tube 315 to the user for inhalation.

Figure 3B:
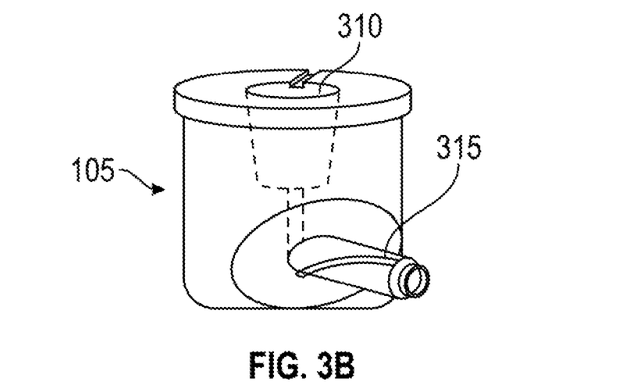
FIG. 3B is a simplified side view of a body of the smoking pipe shown in FIG. 3A without a pipe stem and a mouthpiece receptacle.

FIG. 3B is a simplified side view of a body of the same smoking pipe 300 shown in FIG. 3A without pipe stem 305 and mouthpiece receptacle 130. The figure illustrates that tube 315 can include a quarter turn locking feature.

Figure 3C:
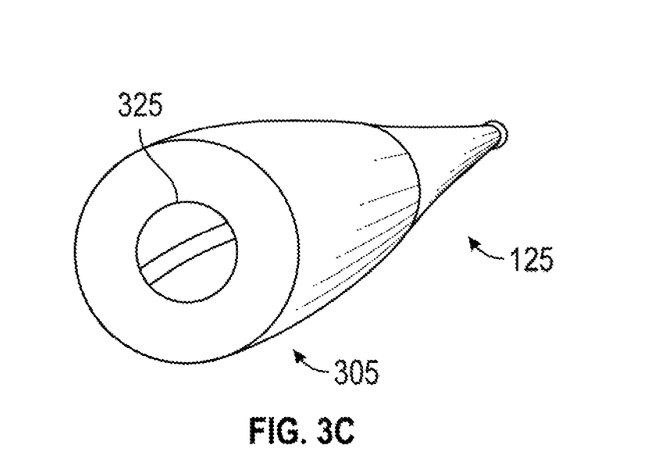
FIG. 3C is a simplified side view of a pipe stem and mouthpiece receptacle for the smoking pipe shown in FIG. 3A.

FIG. 3C is a simplified side view of pipe stem 305 and mouthpiece receptacle 130 for the same smoking pipe 300 shown in FIG. 3A. As shown in this figure, pipe stem 305 includes an opening 325 for receiving tube 315.

Figure 4:
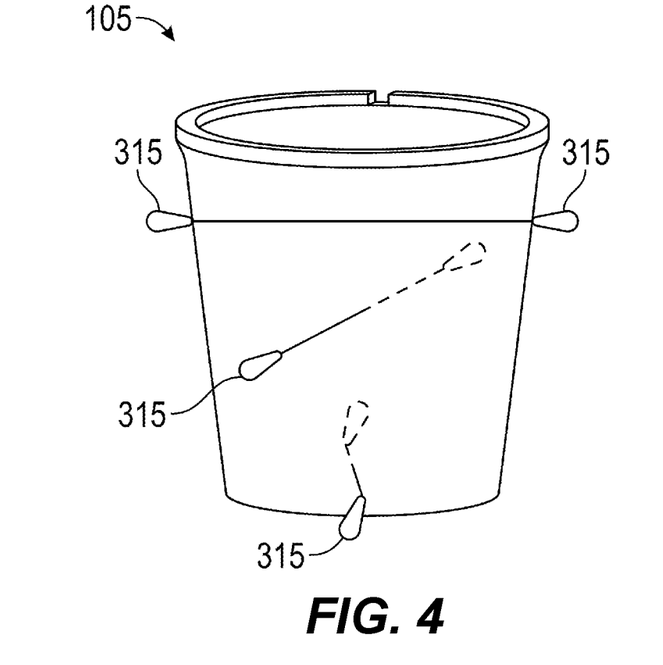
FIG. 4 is a simplified view of a self-contained combustion chamber according to one embodiment.

FIG. 4 is a simplified view of self-contained combustion chamber 105, according to one embodiment. In general, self-contained combustion chamber 105 is a tubular device, cylindrical device, or cone-like device. For example, self-contained combustion chamber 105 has a shape of a paper coffee cup with an opening on its top. Two or more electrodes 315 are provided on the side walls of self-contained combustion chamber 105. Electrodes 315 can be made of any metal suitable for creating an arc of electric discharge. As such, when the material is placed inside self-contained combustion chamber 105, one or more arcs of the electric discharge cause ignition, heating, or combustion of the material. Alternatively, the heating mechanism may generate infrared radiation, conduction or induction through an appropriate contact medium designed to provide the same results as the electric arcs.

Figure 5A:
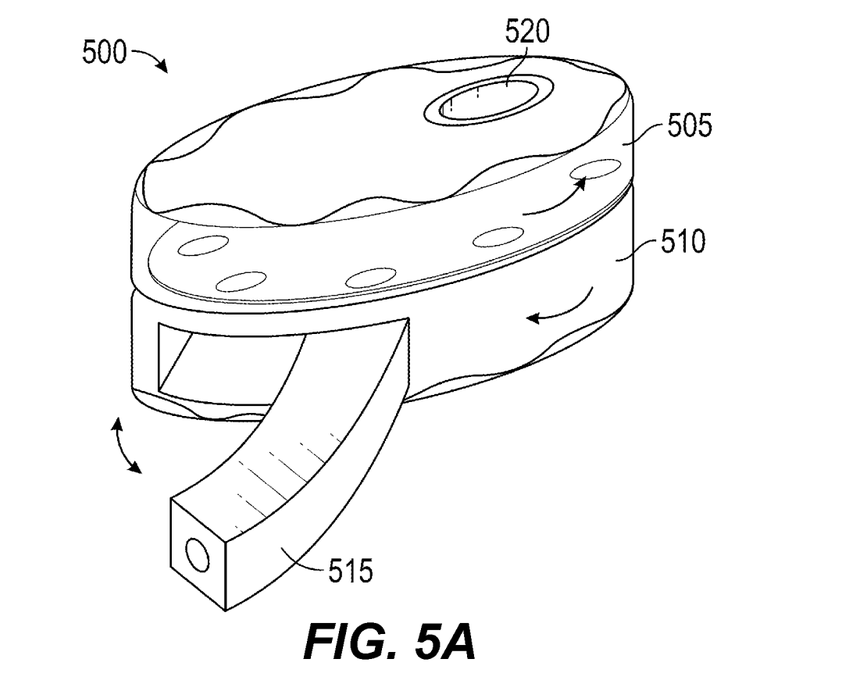
FIG. 5A is a simplified perspective view of a smoking pipe, according to another embodiment.

FIG. 5A is a simplified perspective view of a smoking pipe 500, according to yet another embodiment. Smoking pipe 500 includes two modules 505, 510 that are configured to rotate relative to one another. The top module 505 includes an opening 520 that is connected to a material basket of a combustion chamber. The user can place the material into the combustion chamber through opening 520. The lower module 510 includes a mouth receptacle 515 that is rotatably attached to the lower module 510.

Figure 5B:
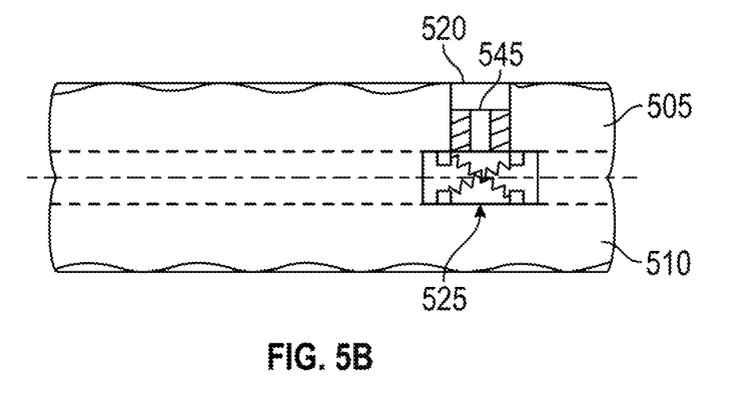
FIG. 5B is a first simplified cross-sectional side view of the smoking pipe shown in FIG. 5A.
Figure 5C:
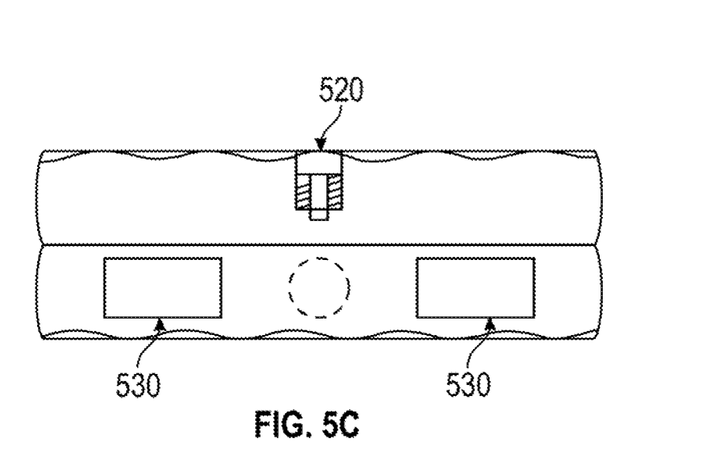
FIG. 5C is a second simplified cross-sectional side view of the smoking pipe shown in FIG. 5A.

FIG. 5B is a first simplified cross-sectional side view of smoking pipe 500 shown in FIG. 5A. This figure shows combustion chamber 525 having two or more electrodes for heating or igniting the material. Combustion chamber 525 is connected to opening 520 via a channel. The channel can include a loader or plunger 545. FIG. 5C is a second simplified cross-sectional side view of smoking pipe 500 shown in FIG. 5A. In this view, there are shown two electrical modules 530 (e.g., controller, processor, or batteries). Alternatively, the heating mechanism may generate infrared radiation, conduction or induction through an appropriate contact medium designed to provide the same results as the electric arcs.

Figure 5D:
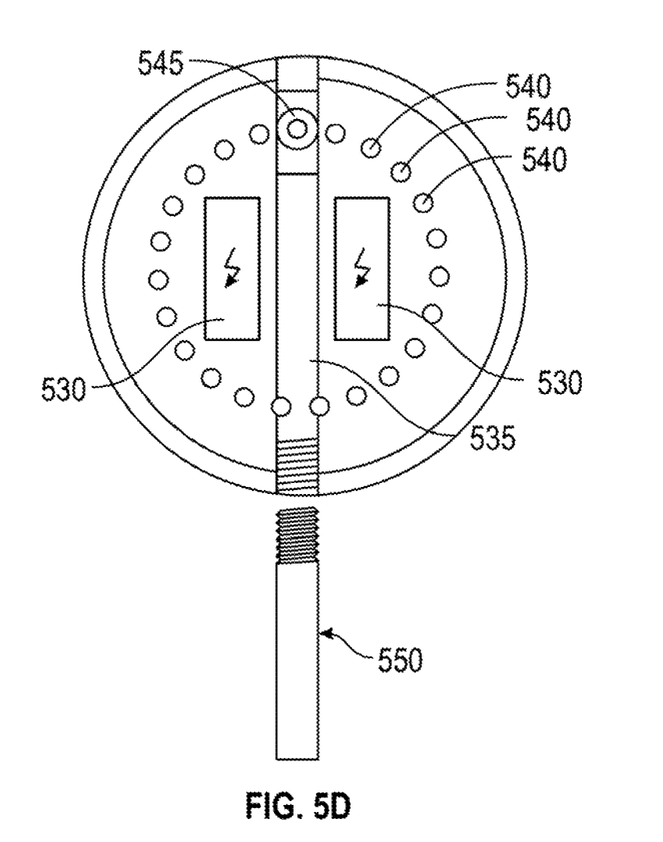
FIG. 5D is a simplified cross-sectional top view of the smoking pipe shown in FIG. 5A.

FIG. 5D is a simplified cross-sectional top view of smoking pipe 500 shown in FIG. 5A. This figure illustrates that a blister pack containing multiple doses 540 of the material can be placed between top module 505 and lower module 510. Upon rotation of top module 505 or lower module 510 around its axis, the blister pack also rotates and places a new dose into combustion chamber 525. The channel between opening 520 and combustion chamber 525 can include loader or plunger 545 to facilitate the insertion or removal of the dose inside combustion chamber 525. FIG. 5D further illustrates an internal tube 535 located substantially at the center of device 500 to cause transportation of the smoke generated inside combustion chamber 525 to a pipe extension 550 or mouthpiece receptacle. The resultant smoke or vapor stream produced by smoking pipe 500 can also be transported to the bong, water pipe, or cannabis pump.

Figure 6A:
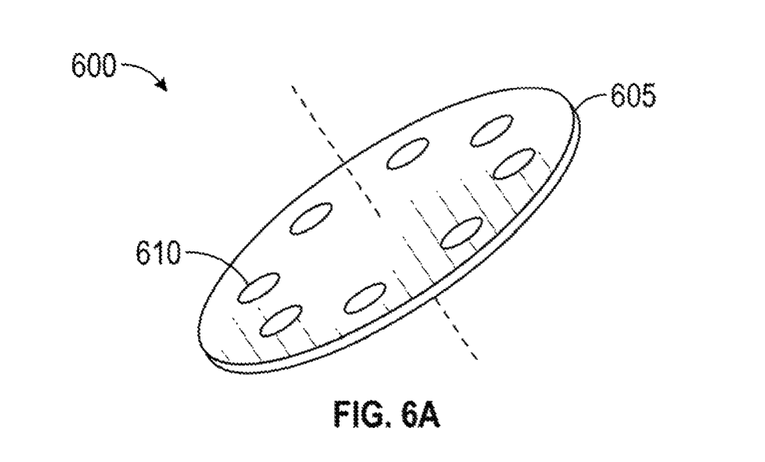
FIG. 6A is a simplified perspective view of a blister pack, according to one embodiment.
Figure 6B:
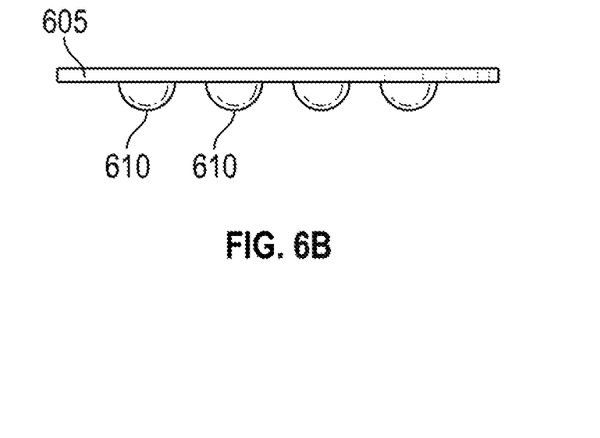
FIG. 6B is a simplified side view of the blister pack shown in FIG. 6A.
Figure 6C:
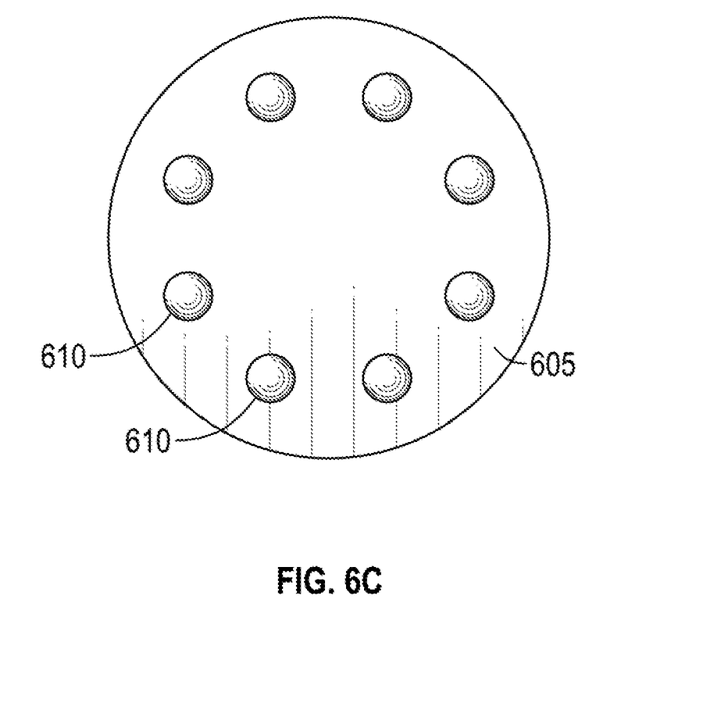
FIG. 6C is a simplified top view of the blister pack shown in FIG. 6A.

FIG. 6A is a simplified perspective view of a blister pack 600, FIG. 6B is a simplified side view of blister pack 600, and FIG. 6C is a simplified top view of blister pack 600. As shown in these figures, blister pack 600 has a disk shape and includes a base 605 and a plurality of slots 610 for placing the material. Each slot 610 containing the material is a "dose" in this embodiment. Slots 610 can have a dome-like design. Base 605 can be made of any suitable polymer material. The doses in blister pack 600 can be of the same or substantially same size and weight.

Figure 7:
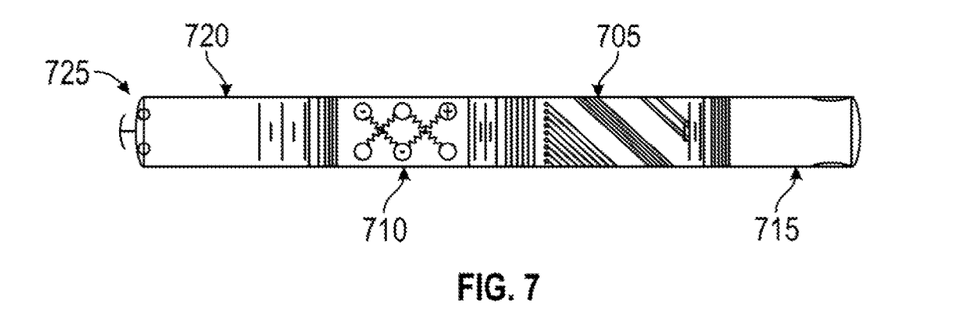
FIG. 7 is a simplified side view of a smoking pipe, according to yet another embodiment.

FIG. 7 is a simplified side view of a smoking pipe 700, according to yet another embodiment. Smoking pipe 700 includes a housing 705 such as a swirl tube (for air induction and particulate separation). Housing 705 can be made of a metal, metal alloy, or polymer material. In this embodiment, housing 705 has a substantially cylindrical or tubular shape. Housing 705 includes a combustion chamber 710 with a plurality of electrodes to cause an electric discharge inside combustion chamber 710. Alternatively, the heating mechanism may generate infrared radiation, conduction or induction through an appropriate contact medium designed to provide the same results as the electric arcs. A material for combustion is to be placed inside combustion chamber 710. Housing 705 also includes a section 720 for containing a rechargeable battery and a programmable electronic control unit. Housing 705 also includes or is connected to a mouthpiece receptacle 715. Finally, a switch 725 is provided in smoking pipe 700 to enable the user to control the programmable electronic control unit and activate/deactivate combustion chamber 710 to cause ignition/heating of the material.

Figure 8:
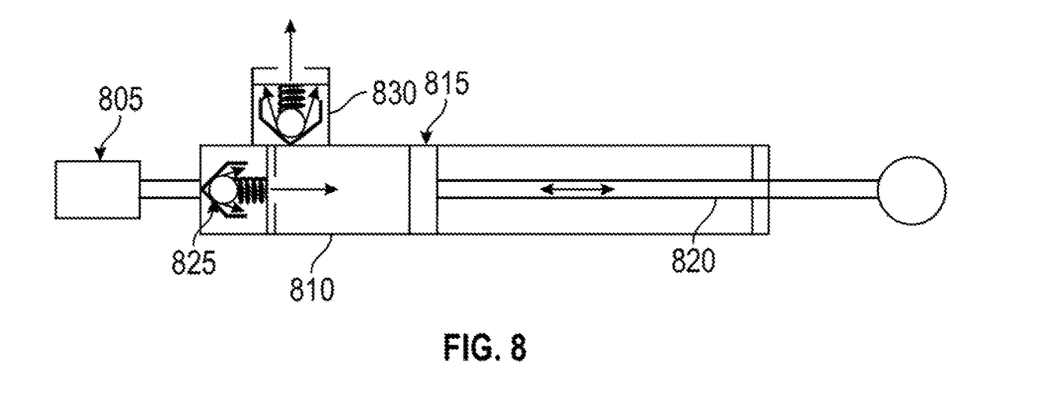
FIG. 8 is a simplified side view of a smoking pump, according to one embodiment.

FIG. 8 is a simplified side view of a smoking pump 800, according to yet another embodiment. Smoking pump 800 includes a combustion chamber 805 and a housing 810, where a piston 815 with a plunger 820 is disposed. Piston 815 is movable within housing 810 when pushed or pulled by a user via plunger 820. Housing 810 has substantially a cylindrical or tubular shape. Combustion chamber 805 is outside of housing 810, but it is connected to housing 810. Smoking pump 800 further includes an inlet check valve 825, which is positioned between combustion chamber 805 and housing 810, and a discharge check valve 830 connected to housing 830. Both inlet check valve 825 and discharge check valve 830 can be controlled by the user to regulate the amount of smoke transferred from combustion chamber 805 inside housing 810 and from housing 810 to the user. Piston 815 can be operated by the user to create a desired vacuum inside the housing 810. The pump device chamber provides for the temporary storage of smoke or vapor for near term use.

Thus, modular smoking devices have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

Figure 9:
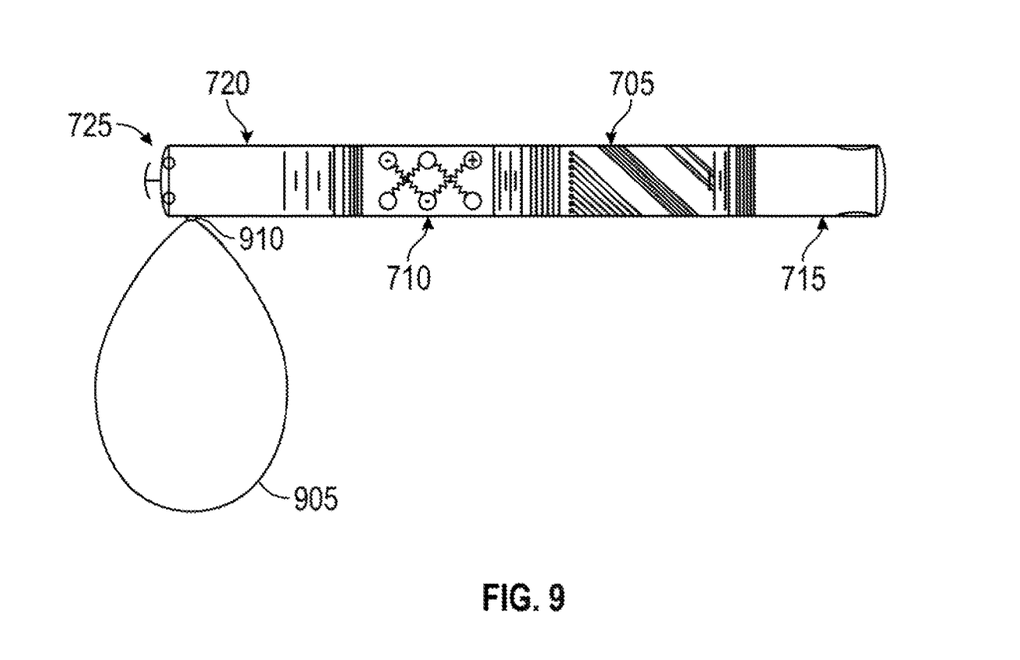
FIG. 9 is a simplified side view of a smoking pump having a hanging device, according to one embodiment.

FIG. 9 is a simplified side view of a smoking pipe 900, according to an example embodiment. The smoking pipe 900 has the same elements as smoking pipe 700 shown on FIG. 7 and is further designed to be worn on a hanging device 905 with a safety breakaway mechanism 910. In an example embodiment, the hanging device 905 may include a chain. The smoking pipe 900 with the hanging device 905 may be used as a neck pipe and may be intended primarily for privacy and covert use when a user can wear the smoking pipe 900 on a user neck. The smoking pipe 900 can be either a vaporizer or combustion pipe and may be intended for one-handed operation for ease of use. Additionally, the heating mechanism may be in the form of electric arc, infrared radiation, conduction, or induction through an appropriate contact medium designed to provide the same repeatable and predictable results for each instance of use.

What is claimed is:

1. A modular device for vaporizing of a material, the device comprising:
   a self-contained vaporization chamber to hold the material, the material having active ingredients for human consumption;
   a vaporization mechanism integrated with the self-contained vaporization chamber, the vaporization mechanism being configured to provide targeted vaporization of the material, wherein upon the vaporization of the material, the active ingredients are consumed by inhaling a vapor resulting from the vaporization, wherein the vaporization mechanism includes at least two pairs of electrodes placed on side walls of the self-contained vaporization chamber; and
   an energy source to power the vaporization mechanism by individually controlling power supplied to each of the at least two pairs of the electrodes and creating an arc of an electric discharge between the electrodes of each of the at least two pairs of the electrodes, the electric discharge passing through the material, wherein the at least two pairs of the electrodes are stacked vertically and rotated with respect to each other.

2. The modular device of claim 1, wherein the self-contained vaporization chamber is designed to receive a prepackaged dose of the material.

3. The modular device of claim 2, wherein the prepackaged dose includes an individual dose of the material.

4. The modular device of claim 2, wherein the prepackaged dose is provided in a blister pack, the blister pack including a plurality of individual doses of the material, the plurality of individual doses including a measured dosage of the material.

5. The module device of claim 4, wherein the blister pack is configured to facilitate dispensing one of the plurality of individual doses into the self-contained vaporization chamber.

6. The modular device of claim 1, further comprising a smoking pipe configured to incorporate the self-contained vaporization chamber and the vaporization mechanism, the smoking pipe being configured to facilitate inhaling the vapor resulting from the vaporization of the material.

7. The modular device of claim 6, wherein the smoking pipe includes a plurality of mouthpiece receptacles for simultaneous consumption of the active ingredients by a plurality of users.

8. The modular device of claim 6, wherein the smoking pipe is constructed of at least one of the following materials: aluminum, stainless steel, glass, polymer material, and a metal alloy.

9. The modular device of claim 1, further comprising a water filtration mechanism to separate the active ingredients in the vapor from undesirable byproducts.

10. The modular device of claim 1, wherein the self-contained vaporization chamber includes a material basket to facilitate manual loading of the material.

11. The modular device of claim 10, wherein the material basket is configured to be heated to heat the material loaded into the material basket.

12. The modular device of claim 1, wherein the energy source includes a rechargeable battery.

13. The modular device of claim 1, further comprising at least one of the following: an activation indicator, a low energy source indicator, an electrical connection indicator, and a mode of operation indicator.

14. The modular device of claim 1, further comprising a safety lockout feature to prevent accidental activation of the self-contained vaporization chamber.

15. The modular device of claim 1, further comprising a pump chamber for temporary storage of vapor for future use.

16. The modular device of claim 1, further comprising a smoking pipe configured to be disassembled for cleaning and maintenance in clinical settings, at home, or remote locations.

17. The modular device of claim 1, wherein the material includes one or more of the following: tobacco, cannabis, a cannabis derivative, a combination of tobacco and cannabis, and a plant-based product.

18. The modular device of claim 1, wherein the material is in one of the following forms: a naturally occurring plant form and a pelletized pharmaceutical form.

\* \* \* \* \*